(12) United States Patent
Mizutani

(10) Patent No.: US 6,649,807 B2
(45) Date of Patent: *Nov. 18, 2003

(54) ABSORBENT ARTICLE

(75) Inventor: Satoshi Mizutani, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/010,467

(22) Filed: Nov. 8, 2001

(65) Prior Publication Data

US 2002/0062112 A1 May 23, 2002

(30) Foreign Application Priority Data

Nov. 21, 2000 (JP) ........................................ 2000-354206

(51) Int. Cl.[7] ................................................. A61F 13/15
(52) U.S. Cl. ..................... 604/367; 604/370; 604/365; 604/378
(58) Field of Search ................................. 604/365, 367, 604/370, 375, 385.01, 383, 378, 380, 385.28

(56) References Cited

U.S. PATENT DOCUMENTS

| | | | | |
|---|---|---|---|---|
| 4,223,677 A | * | 9/1980 | Anderson | 604/365 |
| 4,695,278 A | * | 9/1987 | Lawson | 604/385.27 |
| 5,268,213 A | * | 12/1993 | Murakami et al. | 428/163 |
| 5,490,847 A | * | 2/1996 | Correa et al. | 604/387 |
| 5,591,149 A | * | 1/1997 | Cree et al. | 604/378 |
| 6,066,121 A | * | 5/2000 | Lindquist et al. | 604/385.28 |

FOREIGN PATENT DOCUMENTS

| | | | |
|---|---|---|---|
| EP | 0719531 | 7/1996 | A61F/13/15 |
| EP | 1166731 | 1/2002 | A61F/13/511 |
| JP | 7-500759 | 1/1995 | |
| WO | 91/14414 | 10/1991 | A61F/13/15 |
| WO | WO 93/09745 | 5/1993 | |
| WO | 98/42289 | 10/1998 | A61F/13/15 |
| WO | 1110526 | 6/2001 | A61F/13/512 |

* cited by examiner

Primary Examiner—Weilun Lo
Assistant Examiner—Jacqueline F Stephens
(74) Attorney, Agent, or Firm—Darby & Darby

(57) ABSTRACT

Disclosed is an absorbent article including a sheet which is composed of: a resin layer having a plurality of apertures and forming a liquid-receiving face of the sheet; and a fibrous layer underlying the resin layer. The fibrous layer contains hydrophobic fibers and hydrophilic fibers shorter than the hydrophobic fibers. At least a part of the hydrophilic fibers form aggregates that disperse in the fibrous layer, and at least a part of the aggregates are bonded to the surfaces of the hydrophobic fibers.

9 Claims, 5 Drawing Sheets

ABSORBENT ARTICLE

BACKGROUND OF THE INVENTION

1. Field of the Invention

The present invention relates to an absorbent article capable of absorbing and retaining liquids discharged from the wearer's body such as typically menses, urine and others. More particularly, it relates to an absorbent article which hardly gives a wet feel to the skin of a wearer when a small amount of liquid such as sweat has adhered to its liquid-receiving face.

2. Description of the Related Art

Various absorbent articles such as sanitary napkins, incontinence pads, disposable diapers and others have heretofore been developed and known. These absorbent articles comprise a liquid-impermeable backsheet, a liquid-permeable topsheet, and an absorbent core therebetween.

Regarding the structure of the topsheet of the absorbent articles of those types, for example, there has been known an absorbent article in which a topsheet is formed from a plastic film having apertures. In this absorbent article, liquid given to the surface of the film passes through the apertures and is absorbed by the absorbent core that underlies the film. Since the film is non-absorbent by itself, it can prevent the liquid having been once absorbed by the absorbent core from returning to the surface of the film.

More specifically, when a large amount of liquid is given to the surface of the film of the absorbent article, it passes through the apertures to immediately come into contact with the absorbent core underlying it, so that the liquid on the surface of the film is drawn by the absorbent core owing to the hydrophilic capillary action of the absorbent core. Since the topsheet made of the film is poorly wettable with fluid, it rapidly passes the large amount of liquid through the apertures. Thus, almost all the liquid given thereto is immediately absorbed by the absorbent core.

However, when a small amount of liquid is left on the surface of the topsheet or when sweat of a wearer is adhered thereon, the absorbent core cannot exert its absorbing power on such a small amount of liquid. Therefore, the liquid is liable to remain on the film surface. The small amount of liquid thus remaining on the film surface may be brought into contact with the skin of a wearer or vaporized to stay around it, resulting in a wet or stuffy feel to the skin of a wearer to cause skin roughness. In addition, the topsheet made of the film often sticks to the skin of a wearer, thereby to increase the wet feel.

In Japanese Unexamined Patent Publication (Tokuhyo) No. 500759/1995, on the other hand, there is disclosed an absorbent article in which a fibrous sheet is joined in a screen pattern to the back of a plastic film having apertures. In this absorbent article, a large amount of liquid given to the topsheet smoothly passes through the film and is then distributed to the absorbent core through the fibrous layer. However, it is still difficult to absorb a small amount of liquid left on the surface of the topsheet, sweat adhered thereon and so on.

On the other hand, in the prior art, there have been known absorbent articles having leakage-preventing side walls on the liquid-receiving side thereof, which extend in the longitudinal direction of the article and are positioned on both sides lying opposite one another in the width direction of the article. The leakage-preventing side wall is formed from a nonwoven fabric or the like of hydrophobic synthetic fibers. The nonwoven fabric of hydrophobic synthetic fibers is resistant to liquid permeation therethrough, so that it exhibits the function of preventing leakage of liquid in the width direction as having the ability to return a large amount of liquid having been give thereto to the topsheet of the absorbent article. However, this nonwoven fabric cannot lead a small amount of liquid such as sweat having been adhered thereto to the topsheet, so that the liquid or its vapor will remain between the leakage-preventing side wall and the skin of a wearer, and will give a wet feel to the wearer's skin.

SUMMARY OF THE INVENTION

The present invention has been worked out in view of the shortcoming in the prior art set forth above. It is therefore an object of the present invention to provide an absorbent article which is so designed that a small amount of liquid or its vapor does not remain on its liquid-receiving face in order not to give a wet feel to the skin of a wearer.

According to one aspect of the invention, there is provided an absorbent article comprising a topsheet, a backsheet and an absorbent core positioned between the topsheet and the backsheet, wherein the topsheet includes: a resin layer having a plurality of apertures and forming a liquid-receiving face of the topsheet; and a fibrous layer underlying the resin layer, and the fibrous layer contains hydrophobic fibers and hydrophilic fibers shorter than the hydrophobic fibers, at least a part of the hydrophilic fibers form aggregates that disperse in the fibrous layer, and at least a part of the aggregates are bonded to the surfaces of the hydrophobic fibers. In the topsheet, preferably, the fibrous layer is formed with a plurality of through-holes.

According to another aspect of the invention, there is provided an absorbent article comprising a topsheet, a backsheet and an absorbent core positioned between the topsheet and the backsheet, and having leakage-preventing side walls on a liquid-receiving side of the article, the leakage-preventing side walls extending in a longitudinal direction of the article and lying opposite one another in a width direction of the article, wherein the leakage-preventing side wall includes: a resin layer having a plurality of apertures and forming a liquid-receiving face of the side wall; and a fibrous layer underlying the resin layer, and the fibrous layer contains hydrophobic fibers and hydrophilic fibers shorter than the hydrophobic fibers, at least a part of the hydrophilic fibers form aggregates that disperse in the fibrous layer, and at least a part of the aggregates are bonded to the surfaces of the hydrophobic fibers.

In the fibrous layer, preferably, the fiber density of the hydrophilic fiber aggregates is higher than the fiber density of a portion of the fibrous layer not containing the aggregates therein.

The fibrous layer may contain from 70 to 98% by weight of hydrophobic fibers and from 2 to 30% by weight of hydrophilic fibers.

The hydrophobic fibers may have a length of from 38 to 64 mm, and the hydrophilic fibers may have a length of from 5 to 25 mm. Preferably, the length of the hydrophilic fibers is at most ½ of that of the hydrophobic fibers. If the fiber lengths are within the ranges, the hydrophilic fibers can be readily massed or crimped to form the aggregates and dispersed among the hydrophobic fibers by using a conventional carding unit.

In the absorbent article according to the invention, the liquid-receiving face of the topsheet or side wall is made of the resin layer having the plurality of apertures. Therefore, a large amount of liquid having been given thereto can immediately pass through the apertures therein to thereby prevent the occurrence of residual liquid on the liquid-receiving face. Since the hydrophilic fiber aggregates are dispersed in the fibrous layer underlying the resin layer, on the other hand, when a small amount of liquid, such as sweat of a wearer, or its vapor, is given to the topsheet or side wall, the liquid or vapor can be absorbed by the hydrophilic fiber aggregates so that the liquid-receiving face can be kept always dry.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENTS

The present invention will be discussed hereinafter in detail in terms of the preferred embodiment of an absorbent article according to the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structure are not shown in detail in order to avoid unnecessary obscurity of the present invention.

Figure 1:
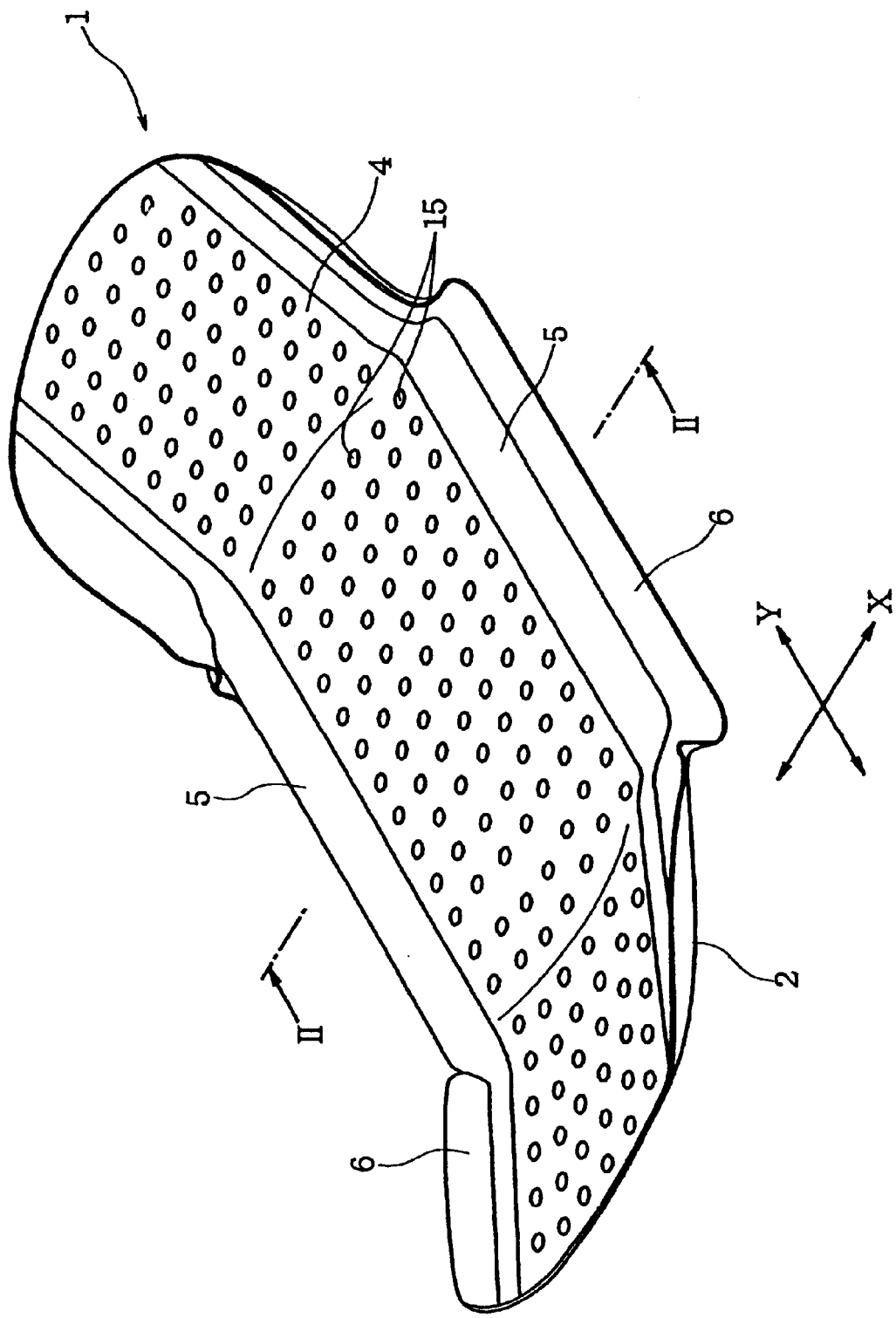
FIG. 1 is a perspective view showing a sanitary napkin as one embodiment of the absorbent article of the invention.
Figure 2:
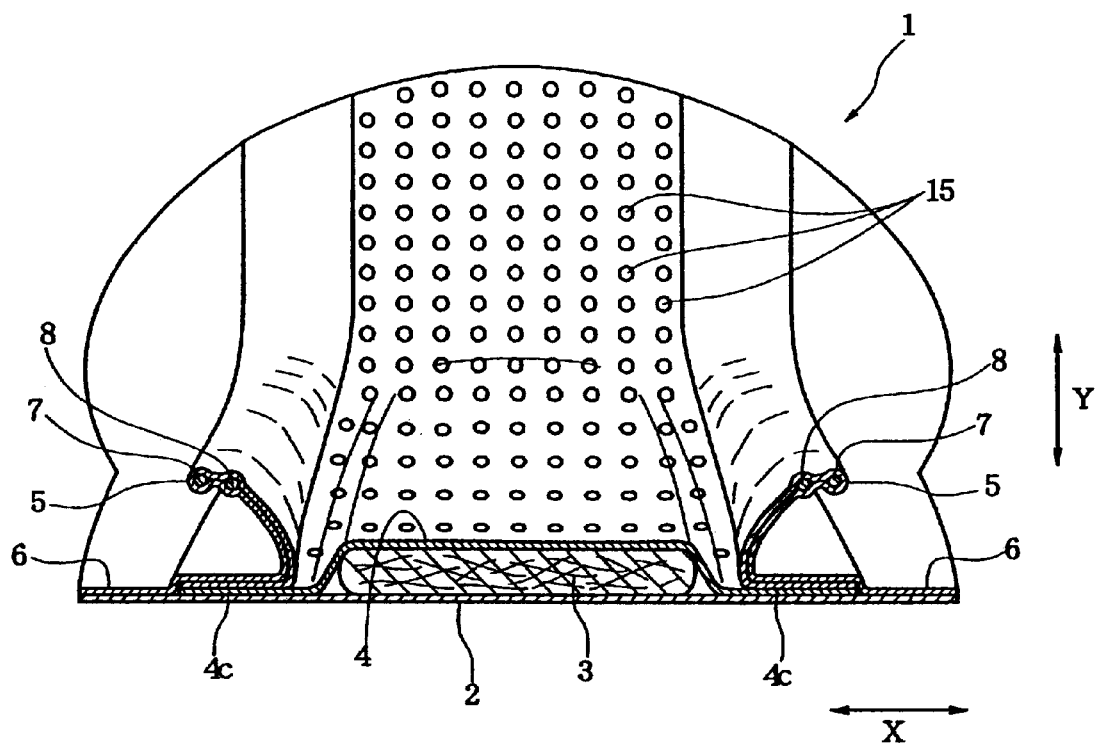
FIG. 2 is a cross-sectional view of the sanitary napkin of FIG. 1, taken along the line II—II.
Figure 3:
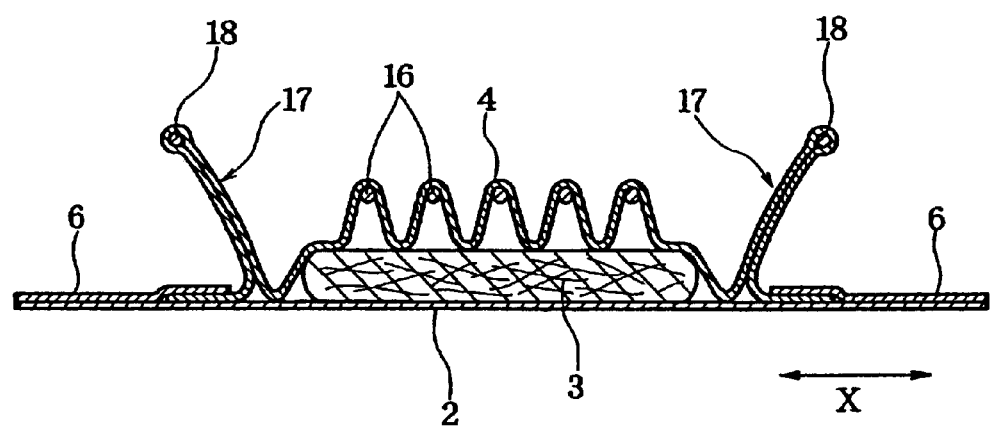
FIG. 3 is a cross-sectional view of another embodiment of a sanitary napkin.
Figure 4:
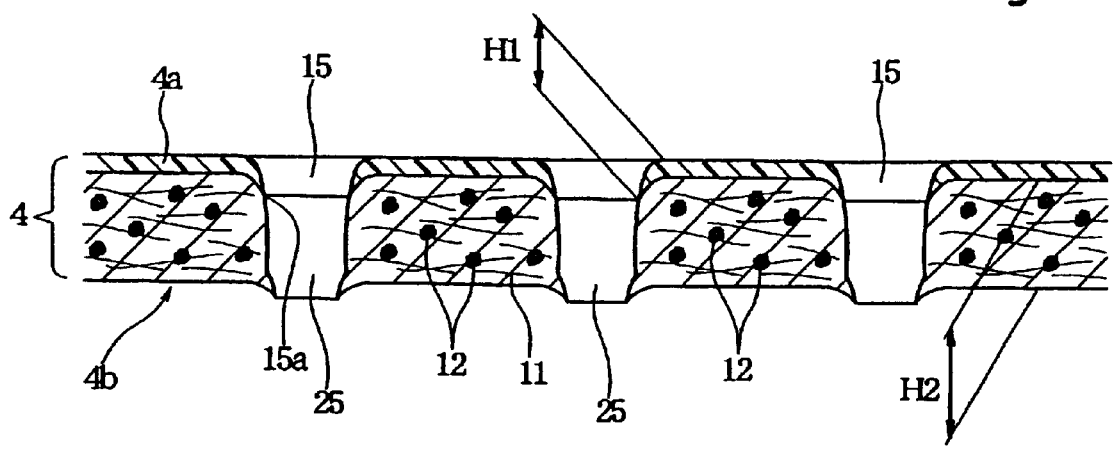
FIG. 4 is an enlarged, schematic cross-sectional view of a portion of a topsheet.
Figure 5:
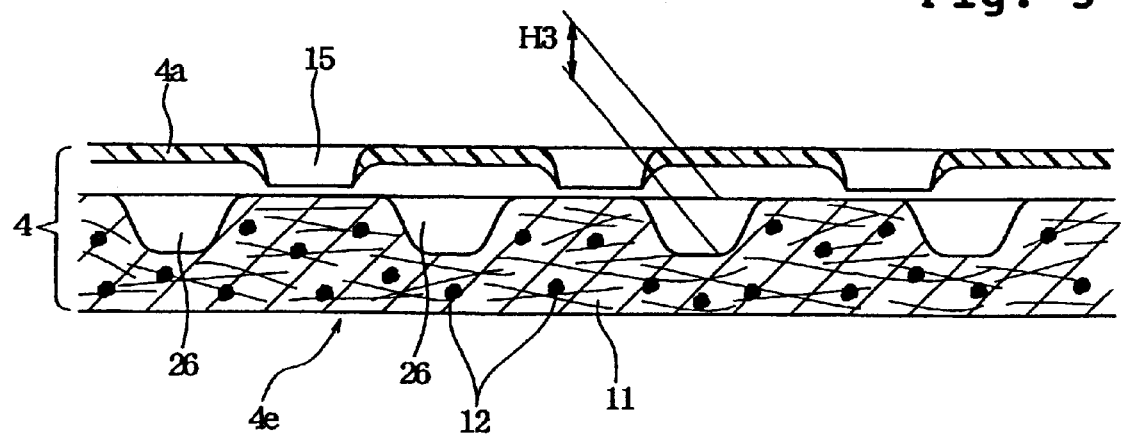
FIG. 5 is an enlarged, schematic cross-sectional view of a portion of another embodiment of a topsheet.
Figure 6:
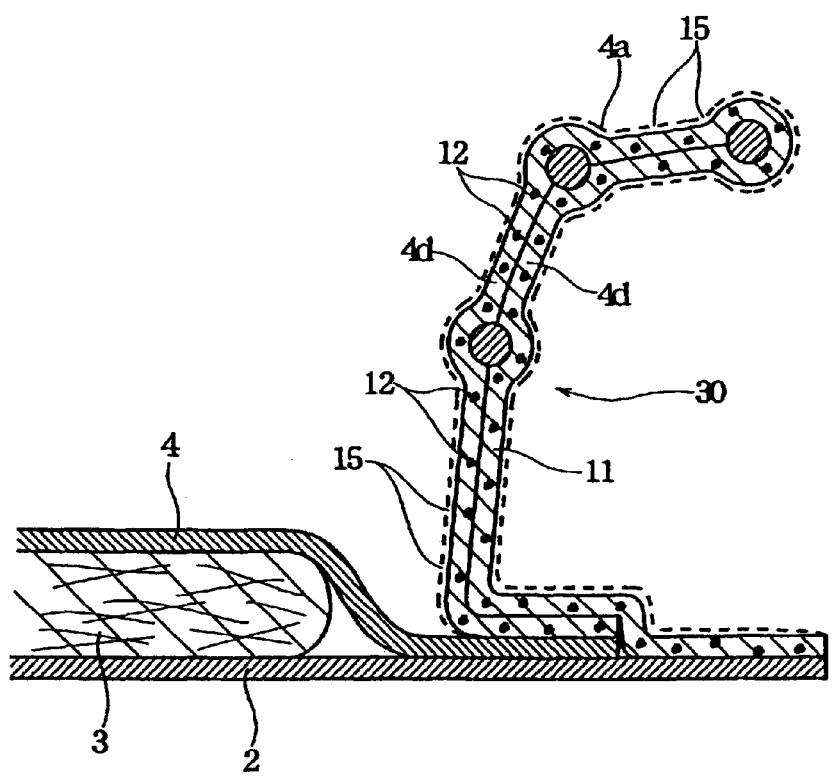
FIG. 6 is a schematic cross-sectional view showing the structure of a leakage-preventing side wall.
Figure 7:
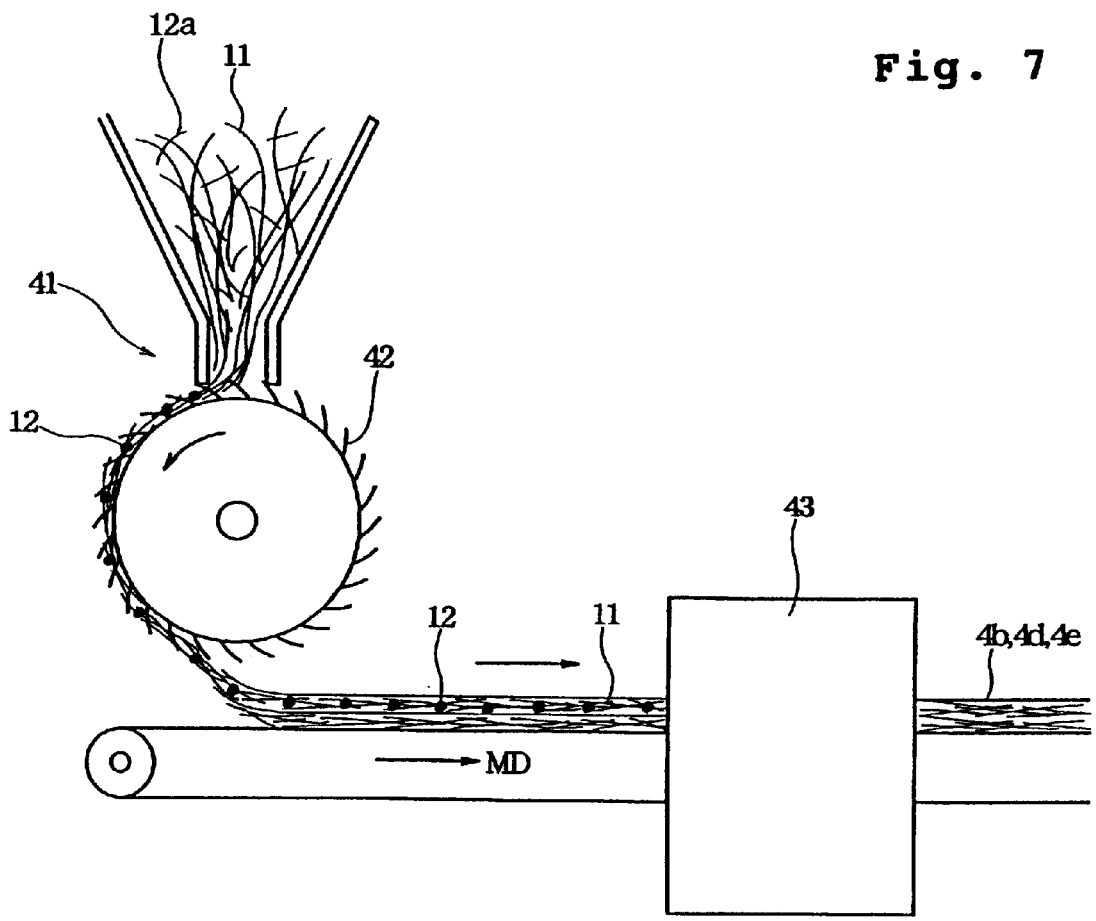
FIG. 7 is an explanatory view showing one example of a method for producing a fibrous layer.

FIG. 1 is a perspective view showing a sanitary napkin 1 as one embodiment of the absorbent article of the invention, which is viewed from its liquid-receiving side; FIG. 2 is a cross-sectional view of FIG. 1, taken along the line II—II; FIG. 3 is a cross-sectional view of another embodiment of a sanitary napkin; FIG. 4 is an enlarged, schematic cross-sectional view of a portion of a topsheet; FIG. 5 is an enlarged, schematic cross-sectional view of a portion of another embodiment of a topsheet; FIG. 6 is a schematic cross-sectional view showing the structure of a leakage-preventing side wall; and FIG. 7 is an explanatory view showing one example of a method for producing a fibrous layer.

The sanitary napkin 1 of FIG. 1 and FIG. 2 comprises a backsheet 2 to be fitted to an external support such as typically an undergarment; an absorbent core 3 which is nearly in the center region, relative to the width direction (X-direction), of the sanitary napkin and which is to absorb liquids discharged from the wearer's body; and a topsheet 4 to cover the liquid-receiving face of the absorbent core 3. Both side portions 4c of the topsheet 4 lying opposite one another in the width direction (X-direction) are joined to the surface of the backsheet 2 outside of the absorbent core 3.

On both sides of the sanitary napkin 1 lying opposite one another in the width direction (X-direction), formed are a pair of leakage-preventing side walls 5 and 5 that extend in the longitudinal direction (Y-direction). In the embodiment shown, each leakage-preventing side wall 5 is formed from one hydrophobic sheet 6.

As shown in FIG. 2, a portion of the hydrophobic sheet 6 is folded into two-layer structure. The two-layer portion of the hydrophobic sheet 6 is provided with two elastic members 7 and 8. Moreover, the two-layer portion of the hydrophobic sheet 6 is further folded outwardly into four-layer structure. The hydrophobic sheet 6 thus folded is joined onto the side portion 4c of the topsheet 4 and onto the backsheet 2 outside of the side portion 4c, except for its portion forming the leakage-preventing side wall 5. In both front and rear end portions in the longitudinal direction (Y-direction) of the sanitary napkin 1, particularly, the hydrophobic sheet 6 is secured on the side portion 4c of the topsheet 4 while being kept in the four-layer structure.

Here, since the elastic members 7 and 8 are joined to the hydrophobic sheet 6 while being stretched in the longitudinal direction (Y-direction), the hydrophobic sheet 6 receives, when the sanitary napkin 1 is in a free condition, longitudinal elastic contractive force of the elastic members 7 and 8 at the top end of the leakage-preventing side wall 5. Owing to the elastic contractive force of the elastic members 7 and 8 acting on the top end of the leakage-preventing side wall 5, the sanitary napkin 1 is, while in a free condition, concavely curved in the longitudinal direction, and, as a result, the leakage-preventing side walls 5 and 5 are to rise toward the skin of a wearer at both sides of the absorbent core 3.

As shown in FIG. 4, the topsheet 4 comprises a resin layer 4a and a fibrous layer 4b, in which the resin layer 4a serves as the liquid-receiving face of the topsheet 4. The resin layer 4a is made of a filmy sheet of synthetic resin, which is hydrophobic or repellent to water, or of which the surface is treated to be hydrophobic or repellent to water, so that the resin layer 4a is impermeable to liquid and is almost non-wettable. For example, it is made from polyethylene, polypropylene, polyester or the like.

As shown in FIG. 4, the resin layer 4a is formed with a plurality of apertures 15 passing through it from one face (upper face) to the other (lower face) of the layer 4a. In the embodiment of FIG. 1, the apertures 15 are aligned in latticework, but are not limited thereto. For example, they may be aligned in any other patterns, for example, in a houndstooth check pattern. Preferably, the area of each aperture 15 falls between 0.2 and 1.13 mm$^2$. Also preferably, the area occupied by all the apertures 15 falls between 40 and 70% of the overall area of the layer 4a. The apertures 15 are formed by needling or the like so that the open end 15a of each aperture 15 protrudes toward the fibrous layer 4b. The thickness (bulkiness), H1, of the resin layer 4a, or that is, the height between the surface of the resin layer 4a and the open end 15a preferably falls between 0.2 and 0.7 mm.

Also preferably, the resin layer 4a contains titanium oxide to be white-opaque. With from 0.5 to 10% by weight of titanium oxide in the resin layer 4a, the topsheet 4 can be white, and it can conceal the blood absorbed by the absorbent core 3.

On the other hand, the fibrous layer 4b is made of a nonwoven fabric which is relatively bulky and contains voids between the constituent fibers, and it comprises hydrophobic synthetic fibers 11 and hydrophilic fiber aggregates 12, as in FIG. 4. The hydrophobic synthetic fibers 11 have a length of from 38 to 64 mm and a fineness of from 2.2 to 6.6 dtex. Hydrophilic fibers 12a for forming the aggregates 12 are natural cellulose fibers of, for example, cotton or rayon, having a length of from 5 to 25 mm and a fineness of from 1.1 to 11 dtex. For the hydrophilic fibers 12a, preferred is cotton.

Figure 8A:
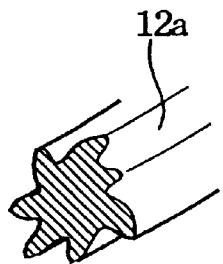
FIG. 8A and FIG. 8B are partially-cut, enlarged perspective views showing preferred cross-sectional profiles of hydrophilic fibers.
Figure 8B:
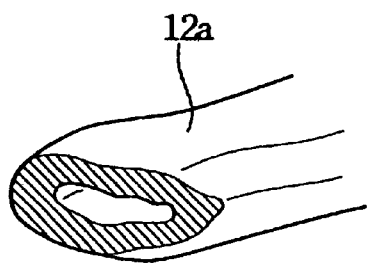

The hydrophilic fibers 12a are of natural cellulose, having a modified cross-section profile as in FIG. 8A or a hollow cross-section profile as in FIG. 8B. For example, they are cotton fibers. The modified cross-section fibers are meant to indicate that their surfaces are not smooth as not having a circular or oval cross section, but their surfaces are modified to have grooves or recesses. The hydrophilic fibers having such modified cross-section profiles have a large surface area to increase liquid absorbing and retaining capacity. Natural cellulose fibers having fibril capillaries are also preferred for the fibrous layer 4b of the topsheet 4, as they can increase liquid absorbing and retaining capacity.

As so mentioned hereinabove and shown in FIG. 4, the shorter hydrophilic fibers 12a are massed or crimped to form aggregates 12 in the layer 4b. The fiber density of the aggregates 12 is higher than that of the hydrophobic synthetic fibers 11 in the portion of the fibrous layer 4b not containing the hydrophilic fiber aggregates 12, and than that of the hydrophobic synthetic fibers 11 and hydrophilic fibers 12a not forming aggregates 12 in the portion of the fibrous layer 4b not containing the hydrophilic fiber aggregates 12 but containing the hydrophilic fibers 12a not forming aggregates 12.

The hydrophilic fiber aggregates 12 are dispersed in the fibrous layer 4b of the topsheet 4, and are held by the hydrophobic synthetic fibers 11 therein. As used herein, the term "hydrophilic fiber aggregate" refers to hydrophilic fibers which are roundly massed or crimped to be entangled together so as to have a higher fiber density than the fiber density of the portion not containing the aggregates therein. Owing to the presence of the hydrophilic fiber aggregates 12, a small amount of liquid or its vapor in the topsheet 4 can be easily retained by the aggregates 12.

Detail of such a sheet comprising mainly hydrophobic fibers and having hydrophilic fiber aggregates dispersed therein has been disclosed in commonly owned co-pending U.S. patent application Ser. No. 09/883,970. Disclosure of the above-identified commonly owned co-pending application is herein incorporated by reference.

At least the surface of the hydrophobic synthetic fibers 11 is formed from a low-melting-point material. Preferably, they are core/sheath-structured bicomponent fibers in which the core is PP (polypropylene) or PET (polyethylene terephthalate) and the sheath is PE (polyethylene). They may also be PE fibers, but preferred are the above-mentioned core/sheath-structured bicomponent fibers in which the core is made of PP or PET to have a high stiffness, for ensuring good voids in the fibrous layer 4b. If desired, the hydrophobic synthetic fibers 11 may be coated with a surfactant that makes them hydrophilic. However, when a large amount of liquid is given to the surfactant-coated fibers, the surfactant will flow away and the fibers could not be hydrophilic.

The fibrous layer 4b is made of a thermal-bonded nonwoven fabric, preferably that produced in a through-air bonding process. In this, the hydrophobic synthetic fibers 11 are thermally fused together, and the hydrophilic fiber aggregates 12 of cotton or the like are secured to the surfaces of the hydrophobic synthetic fibers 11, as the surfaces exhibit fusion bonding force in molten or semi-molten condition. This results in having a sufficient bulkiness as well as a good cushioning property.

In order that the hydrophilic fiber aggregates 12 are surely held in the fibrous layer 4b, it is desirable that the hydrophobic synthetic fibers 11 therein are long in some degree and that the fibrous layer 4b has a sheet structure in which the hydrophilic fiber aggregates 12 can be readily secured on the surfaces of the hydrophobic synthetic fibers 11. For example, in a point-bonded nonwoven fabric of heat-fusible short fibers, the hydrophilic fiber aggregates 12 could not be surely held among the hydrophobic synthetic fibers 11 and will readily drop off. A spun-laced nonwoven fabric in which the constituent fibers are entangled by water jets, and a chemical-bonded nonwoven fabric in which the constituent fibers are bonded together by chemical bonding force are not bulky, and their internal porosity is low. Therefore, a large amount of liquid given to the topsheet 4 is difficult to pass through the space between the hydrophobic synthetic fibers 11 toward the absorbent core 3. Accordingly, as so mentioned hereinabove, the fibrous layer 4b is preferably made of a thermal-bonded nonwoven fabric produced in a through-air bonding process. Alternatively, the thermal-bonded nonwoven fabric for the fibrous layer 4b may be heated with a heat roller instead of hot air. A spun-bonded nonwoven fabric of heat-fusible filaments is also usable for the fibrous layer 4b.

As so mentioned hereinabove, it is desirable that the fibrous layer 4b of the topsheet 4 has a suitable degree of porosity in order that a large amount of liquid given to the topsheet 4 can smoothly pass through the space between the hydrophobic synthetic fibers 11 toward the absorbent core 3 that underlies the topsheet 4. To that effect, therefore, the basis weight of the fibrous layer 4b preferably falls between 20 and 60 g/m$^2$, and the thickness (bulkiness), H2, of the fibrous layer 4b preferably falls between 0.2 and 10 mm, more preferably between 0.3 and 2 mm. When a large amount of liquid is given to the topsheet 4, it can smoothly pass through the space between the hydrophobic synthetic fibers 11 and can be readily absorbed by the absorbent core 3, if the basis weight and the thickness of the fibrous layer 4b are defined to fall within the ranges as above.

In order that a large amount of liquid given to the topsheet 4 can smoothly pass through the space between the hydrophobic synthetic fibers 11 to reach the absorbent core 3, it is also desirable that the hydrophilic fiber aggregates 12 are suitably dispersed among the hydrophobic synthetic fibers 11 in the fibrous layer 4b. Also preferably, the fibrous layer 4b of the topsheet 4 contains from 70 to 98% by weight of the hydrophobic synthetic fibers 11 and from 2 to 30% by weight of the hydrophilic fibers 12a, some in the form of the aggregates 12 and others in the non-aggregated form. More preferably, the hydrophilic fibers 12a account for from 2 to 10% by weight of the fibrous layer 4b.

Also preferably, the aggregates 12 of massed or crimped hydrophilic fibers 12a are uniformly dispersed in the fibrous layer 4b, spaced from each other by a predetermined distance. It is desirable that the hydrophilic fiber aggregates 12 are uniformly distributed throughout the fibrous layer 4b from its face to back, but in order that a small amount of liquid, such as sweat, having adhered to the surface of the resin layer 4a or its vapor can be effectively absorbed by the hydrophilic fiber aggregates 12, a larger amount of the hydrophilic fiber aggregates 12 may be dispersed in the part of the fibrous layer 4b nearer to the resin layer 4a with no aggregates 12 being in the part thereof nearer to the absorbent core 3.

As shown in FIG. 4, the fibrous layer 4b has a large number of through-holes 25 formed therein. With the through-holes 25, the fibrous layer 4b can have capillaries communicating to the absorbent core 3, and a large amount of liquid given to the topsheet 4 can smoothly pass through the apertures 15 in the resin layer 4a and through the through-holes 25 in the fibrous layer 4b to be readily absorbed by the absorbent core 3.

For forming the through-holes 25 therein, the fibrous layer 4b is preferably perforated by needling or the like so that the fibers in the inner surface of each through-hole 25 can protrude toward the absorbent core 3 that underlies the fibrous layer 4b. Having the through-holes 25 formed therein, the fibrous layer 4b can be bulkier. Preferably, the apertures 15 in the resin layer 4a and the through-holes 25 in the fibrous layer 4b are simultaneously formed by needling so that adjacent aperture 15 and through-hole 25 thus formed communicate to each other, as shown in FIG. 4. However, the combined structure of the resin layer 4a and the fibrous layer 4b is not limited to the illustrated one. As the case may be, the apertures 15 may be shifted from the through-holes 25. It is desirable that the diameter of the through-holes 25 falls between 0.3 and 2.0 mm and that the area occupied by the through-holes 25 in the fibrous layer 4b falls between 5 and 60%. If the diameter of the through-holes and the area occupied by the through-holes are smaller than the defined ranges, the liquid permeability through the fibrous layer 4b will be poor; but if larger than them, the phenomenon referred to as "wet back", in which the liquid having been once absorbed by the absorbent core 3 returns to the topsheet 4, will occur to give a wet feel to the skin of a wearer.

The resin layer 4a and the fibrous layer 4b may be partially or entirely joined together by thermally fusing them or applying a hot-melt type adhesive. Alternatively, a molten resin for the resin layer 4a may be applied to the surface of the fibrous layer 4b in a mode of melt lamination to thereby integrate the resin layer 4a and the fibrous layer 4b.

The backsheet 2 of the sanitary napkin 1 is formed from a liquid-impermeable sheet. For this backsheet 2, usable is any of an air-permeable (breathable) resin film, a spun-bonded or spun-laced nonwoven fabric specifically processed for water repellency, and a nonwoven fabric of which the back is laminated with an air-permeable resin film. Preferably, an adhesive layer is disposed on the back of the backsheet 2, via which the sanitary napkin 1 is secured on an external support such as an undergarment; and the adhesive layer is preferably coated with a released paper (or separate paper) that protects it until use of the sanitary napkin 1.

The absorbent core 3 is made of ground pulp or a mixture of ground pulp and a superabsorbent polymer. Concretely, ground pulp or a mixture of ground pulp and a superabsorbent polymer is wrapped with an absorbent sheet such as tissue paper.

The hydrophobic sheet 6 to form the leakage-preventing side wall 5 is hydrophobic or repellent to water, and it may be made of a melt-blown nonwoven fabric, a through-air bonded nonwoven fabric, a point-bonded nonwoven fabric, an air-laid nonwoven fabric, or a composite laminate of a spun-bonded nonwoven fabric and a melt-blown nonwoven fabric. It may also be made of a resin film, or a laminate of a nonwoven fabric and a resin film.

The liquid-permeable function of the topsheet 4 of the sanitary napkin 1 is described below.

As has been described heretofore, the topsheet 4 is a laminate of the hydrophobic or water-repellent resin layer 4a, and the fibrous layer 4b of a nonwoven fabric consisting essentially of hydrophobic synthetic fibers 11 and having a relatively large degree of porosity with hydrophilic fiber aggregates 12 being dispersed therein. When the topsheet 4 has received a large amount of liquid such as menses, the large amount of liquid penetrates through the apertures 15 and the through-holes 25 and immediately reaches the absorbent core 3. The absorbent core 3 draws and absorbs the large amount of liquid owing to its hydrophilic capillary action. Here, the surfaces of the hydrophobic synthetic fibers 11 are poorly resistant to the liquid penetration, and therefore, the liquid can rapidly pass through the space between the hydrophobic synthetic fibers 11 to be absorbed by the absorbent core 3. More specifically, the aggregates 12 are dispersed in the fibrous layer 4b, while spaced from each other, so that the liquid can rapidly pass through the space between the hydrophobic synthetic fibers 11 in the portion not containing the aggregates 12, to be absorbed by the absorbent core 3. In case where the large amount of liquid passes through the topsheet 4, the hydrophilic fiber aggregates 12 dispersed therein will receive a part of the liquid. In this case, however, the greater part of the liquid is drawn by the absorbent core 3 owing to the hydrophilic capillary action of the absorbent core 3, and only a small part of the liquid will be retained by the hydrophilic fiber aggregates 12.

When a small amount of liquid is given to the topsheet 4, on the other hand, since the hydrophilic fiber aggregates 12 in the massed or crimped condition have a higher fiber density, the small amount of liquid is well retained by the aggregates 12 so that the surface of the topsheet 4 can be kept dry. Specifically, when an extremely small amount of liquid is applied to the topsheet 4, or when a little sweat is given thereto from the skin of a wearer, or when the wearer's sweat has vaporized owing to the wearer's body temperature to stay in the topsheet 4, the small amount of liquid or vapor is drawn and retained by the hydrophilic fiber aggregates 12 dispersed in the fibrous layer 4b, through the apertures 15. Since the hydrophilic fiber aggregates 12 are dispersed in the massed or crimped condition to have a higher density, the liquid or vapor is readily drawn by the hydrophilic fiber aggregates 12 and the liquid or vapor thus drawn is well retained by the hydrophilic fiber aggregates 12.

In addition, since the surface of the fibrous layer 4b is coated with the resin layer 4a, the liquid thus retained by the hydrophilic fiber aggregates 12 hardly returns to the surface of the topsheet 4. Accordingly, the surface of the topsheet 4 is kept dry, and does not give a wet or stuffy feel to the skin of a wearer.

FIG. 5 shows another embodiment of the topsheet 4.

In the topsheet 4 of the embodiment of FIG. 5, the resin layer (resin film) 4a having the apertures 15 is partially joined to a fibrous layer 4e. This fibrous layer 4e is so processed as to have recesses 26 in its surface opposite to that adjacent to the absorbent core 3. The depth, H3, of the recesses 26 preferably falls between 0.1 and 1 mm, and the area occupied by the recesses 26 preferably falls between 3 and 30% of the surface area of the fibrous layer 4e. If they exceed the preferred ranges, the contact area between the resin layer 4a and the fibrous layer 4e will be reduced to lower liquid permeability and absorbency.

Like the fibrous layer 4b in FIG. 4, the fibrous layer 4e in the embodiment of FIG. 5 may be formed from a through-air bonded nonwoven fabric containing the hydrophobic synthetic fibers 11 and the hydrophilic fiber aggregates 12. The recesses 26 can be formed by heating and pressing the nonwoven fabric with an embossing roll.

In the fibrous layer 4e, the fiber density of the portions processed to form the recesses 26 is increased, so that the fiber density of the remaining portion becomes relatively lower. Accordingly, a large amount of liquid having passed through the apertures 15 of the resin layer 4a passes through the portion of the fibrous layer 4e having a lower density while being drawn by the capillary action of the absorbent core 3, and is thereby absorbed by the absorbent core 3. On the other hand, a small amount of liquid such as sweat having adhered to the surface of the resin layer 4a or its vapor is drawn by the aggregates 12. Specifically, the small amount of liquid or its vapor is led to the higher density portions of the fibrous layer 4e processed to form the recesses 26, and on the way to the higher density portions, it is absorbed by the aggregates 12. Thus, the small amount of liquid or its vapor can be readily retained by the aggregates 12.

With the fibrous layer 4e processed as in FIG. 5, its air permeability and cushioning property can be increased. In addition, increasing the surface area of the layer 4e to come into contact with the liquid results in increased liquid absorbency.

It should be noted that the fibrous layer 4e of FIG. 5 may also be formed with the through-holes 25.

The sanitary napkin having the topsheet 4 of FIG. 4 or FIG. 5 may be fabricated in a different manner, for example, as in FIG. 3 that shows a cross section of a different type of sanitary napkin.

In the sanitary napkin of the type of FIG. 3, the topsheet 4 is so corrugated above the absorbent core 3 as to have hills and valleys alternated in the width direction (X-direction). At the top of each hill, provided is an elastic member 16 that extends in the longitudinal direction (Y-direction). While kept stretched in the longitudinal direction, the elastic member 16 is joined to the topsheet 4. Accordingly, owing to the elastic contractive force of the elastic member 16, the top of each hill is raised and spaced away from the absorbent core 3, so that the substantial bulkiness of the topsheet 4 is thereby increased.

The height of the hills of the corrugated topsheet 4 preferably falls between 0.5 and 5 mm, and the pitch of the hills in the width direction preferably falls between 0.5 and 10 mm.

As shown in FIG. 3, moreover, both side portions of the topsheet 4 lying opposite one another in the width direction are raised from the backsheet 2, and at the top end of each rising side portion of the topsheet 4, provided is an elastic member 18 extending in the longitudinal direction. Thus, there are formed leakage-preventing side walls 17 of the topsheet 4. In this embodiment, the hydrophobic sheets 6 are provided outside of the side walls 17 to cover the side edges of the topsheet 4.

FIG. 6 shows still another embodiment of the invention, in which a leakage-preventing side wall 30 of a sanitary napkin is formed from a composite sheet composed of a resin layer 4a and a fibrous layer 4d.

The composite sheet for the leakage-preventing side wall 30 is formed by putting the resin layer (resin film) 4a on the fibrous layer 4d. The resin layer 4a has the apertures 15 formed therein like in FIG. 4 and FIG. 5; and the fibrous layer 4d is made of a nonwoven fabric, such as through-air bonded nonwoven fabric, in which the hydrophilic fiber aggregates 12 are dispersed among the hydrophobic synthetic fibers 11. Preferably, the fibrous layer 4d and the resin layer 4a are at least partially joined to each other. In this embodiment, it is desirable that the fibrous layer 4d does not have through-holes such as those shown in FIG. 4, but the fibrous layer 4d may have the recesses 26 shown in FIG. 5.

This leakage-preventing side wall 30 is resistant to liquid permeation through it, because its surface is made of the resin layer 4a and the fibrous layer 4d comprises mainly the hydrophobic synthetic fibers 11. Therefore, a large amount of liquid having been given to the surface of the leakage-preventing side wall 30 is blocked by the surface of the resin layer 4a, so that the liquid is prevented from leaking in the width direction of the sanitary napkin.

On the other hand, a small amount of liquid such as sweat having adhered to the surface of the resin layer 4a of the leakage-preventing side wall 30 or its vapor passes through the apertures 15 of the resin layer 4a to be absorbed by the hydrophilic fiber aggregates 12 in the fibrous layer 4d. Accordingly, the surface of the leakage-preventing side wall 30 is prevented from having a wet feel, and hardly gives a stuffy feel to a wearer.

FIG. 7 shows one example of a method for producing the fibrous layers 4b, 4d and 4e shown in FIGS. 4, 5 and 6.

In the production method of FIG. 7, hydrophobic synthetic fibers 11 having a length of from 38 to 64 mm and hydrophilic fibers 12a (of cotton) having a length of from 5 to 25 mm are fed into a carding unit 41, and are opened by the pins 42 standing around a rotary roll. Because the hydrophobic synthetic fibers 11 are satisfactorily long and stiff, they are aligned in the machine direction (MD) owing to the opening force of the pins 42. On the other hand, however, the hydrophilic fibers 12a are short and especially those of cotton are not stiff but flexible. Therefore, when receiving the opening force of the pins 42, they are not aligned in MD and most of them are massed or crimped to form the aggregates 12, which are held between the pins 42. As a result, there are formed a fibrous web in which the hydrophilic fiber aggregates 12 are dispersed among the hydrophobic synthetic fibers 11 aligned in MD. The fibrous web is then conveyed to a through-air system heating chamber 43, in which the hydrophobic synthetic fibers 11 in the fibrous web are thermally bonded and the hydrophilic fiber aggregates 12 therein are secured to the fused surfaces of the hydrophobic synthetic fibers 11. As a result, the fibrous web is formed into a nonwoven fabric for the fibrous layers 4b, 4d, 4e.

In place of the heating chamber 43, a hot roll may be used for thermally bonding the hydrophobic synthetic fibers 11 in the fibrous web.

In the absorbent article of the invention, as described in detail hereinabove, the sheet composed of the resin layer and the fibrous layer is used for forming the topsheet and/or leakage-preventing side wall. When the topsheet is formed from the sheet composed of the resin layer and the fibrous layer, a large amount liquid given thereto immediately passes through it to be absorbed by the absorbent core underlying the topsheet. A small amount of liquid or its vapor given to the resin layer, on the other hand, readily migrates to the fibrous layer through the apertures to be retained by the hydrophilic fiber aggregates. Accordingly, the surface of the topsheet can be kept dry so as not to give a wet feel to the skin of a wearer, and therefore an ill effect such as the occurrence of skin roughness can be eliminated.

When the leakage-preventing side wall is formed from the sheet composed of the resin layer and the fibrous layer, on the other hand, a large amount of liquid given to the absorbent article is prevented from leaking in the width direction, while a small amount of liquid given to the surface of the leakage-preventing side wall or its vapor is prevented from remaining thereon. This results in prevention of a wet or stuffy feel which would otherwise occur in a skin-contacting portion of the leakage-preventing side wall.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article comprising a topsheet, a backsheet and an absorbent core positioned between the topsheet and the backsheet, wherein
the topsheet includes: a resin layer having a plurality of apertures and forming a liquid-receiving face of the topsheet; and a fibrous layer underlying the resin layer, and
the fibrous layer contains hydrophobic synthetic fibers and hydrophilic fibers shorter than the hydrophobic fibers, and at least a part of the hydrophilic fibers are formed into aggregates, wherein the aggregates are separate from each other and are uniformly dispersed in the fibrous layer, and are bonded to surfaces of the hydrophobic fibers.

2. The absorbent article as set forth in claim 1, wherein the fibrous layer is formed with a plurality of through-holes.

3. The absorbent article as set forth in claim 1, wherein a fiber density of the aggregates is higher than a fiber density of a portion of the fibrous layer without the aggregates.

4. The absorbent article as set forth in claim 1, wherein the fibrous layer contains from 70 to 98% by weight of hydrophobic fibers and from 2 to 30% by weight of hydrophilic fibers.

5. The absorbent article as set forth in claim 1, wherein the hydrophobic fibers have a length of from 38 to 64 mm, and the hydrophilic fibers have a length of from 5 to 25 mm.

6. An absorbent article comprising a topsheet, a backsheet and an absorbent core positioned between the topsheet and the backsheet, and having leakage-preventing side walls on a liquid-receiving side of the article, the leakage-preventing side walls extending in a longitudinal direction of the article and lying opposite one another in a width direction of the article, wherein
the leakage-preventing side wall includes: a resin layer having a plurality of apertures and forming a liquid-receiving face of the side wall; and a fibrous layer underlying the resin layer, and
the fibrous layer contains hydrophobic synthetic fibers and hydrophilic fibers shorter than the hydrophobic fibers, and at least a part of the hydrophilic fibers are formed into aggregates, wherein the aggregates are separate from each other and are uniformly dispersed in the fibrous layer, and are bonded to surfaces of the hydrophobic fibers.

7. The absorbent article as set forth in claim 6, wherein the fiber density of the hydrophilic fiber aggregates is higher than the fiber density of a portion of the fibrous layer not containing the aggregates therein.

8. The absorbent article as set forth in claim 6, wherein the fibrous layer contains from 70 to 98% by weight of hydrophobic fibers and from 2 to 30% by weight of hydrophilic fibers.

9. The absorbent article as set forth in claim 6, wherein the hydrophobic fibers have a length of from 38 to 64 mm, and the hydrophilic fibers have a length of from 5 to 25 mm.

* * * * *